(12) United States Patent
Koutsky et al.

(10) Patent No.: US 9,025,831 B2
(45) Date of Patent: May 5, 2015

(54) APPARATUS AND METHODS FOR AUTOMATED PHENOTYPIC SCREENING OF PLANT GENOTYPES

(75) Inventors: Keith A. Koutsky, Durham, NC (US); Susan R. Norris, University City, MO (US); James V. O'Brien, Mystic, CT (US); Douglas Boyes, Verona, WI (US)

(73) Assignee: Monsanto Technology LLC, St. Louis, MO (US)

( * ) Notice: Subject to any disclaimer, the term of this patent is extended or adjusted under 35 U.S.C. 154(b) by 482 days.

(21) Appl. No.: 12/943,516

(22) Filed: Nov. 10, 2010

(65) Prior Publication Data

US 2011/0135161 A1 Jun. 9, 2011

Related U.S. Application Data

(60) Provisional application No. 61/259,819, filed on Nov. 10, 2009.

(51) Int. Cl.
*G06K 9/00* (2006.01)
*A01H 1/04* (2006.01)
*G01N 33/00* (2006.01)

(52) U.S. Cl.
CPC .............. *A01H 1/04* (2013.01); *G01N 33/0098* (2013.01)

(58) Field of Classification Search
USPC .......................... 382/110; 348/135; 47/17, 65
See application file for complete search history.

(56) References Cited

U.S. PATENT DOCUMENTS

| | | | |
|---|---|---|---|
| 3,824,736 A * | 7/1974 | Davis | 47/17 |
| 5,361,534 A * | 11/1994 | Burns et al. | 47/79 |
| 5,394,646 A * | 3/1995 | Sumiyoshi et al. | 47/17 |
| 6,184,988 B1 * | 2/2001 | Ferrari | 356/428 |
| 7,367,458 B2 * | 5/2008 | Leyns et al. | 209/551 |
| 7,697,133 B2 | 4/2010 | Leyns et al. | |
| 7,845,111 B2 | 12/2010 | Dillen et al. | |
| 7,866,091 B2 | 1/2011 | Dillen et al. | |
| 7,972,221 B2 * | 7/2011 | Furze et al. | 473/151 |
| 8,209,903 B2 | 7/2012 | Dillen et al. | |
| 2004/0200146 A1 * | 10/2004 | Leyns et al. | 47/65 |
| 2004/0237386 A1 * | 12/2004 | Madsen et al. | 47/1.01 P |
| 2005/0183389 A1 * | 8/2005 | Craig et al. | 53/397 |
| 2006/0150497 A1 * | 7/2006 | Kaprielian | 47/62 R |
| 2007/0044445 A1 * | 3/2007 | Spicer et al. | 56/10.1 |
| 2007/0186313 A1 * | 8/2007 | Lightner et al. | 800/320.1 |
| 2007/0272098 A1 * | 11/2007 | Lutz | 101/35 |
| 2007/0289211 A1 * | 12/2007 | Lejeune et al. | 47/65 |
| 2008/0002185 A1 * | 1/2008 | Gitelson et al. | 356/73 |
| 2008/0010703 A1 * | 1/2008 | Creelman et al. | 800/289 |
| 2008/0253618 A1 * | 10/2008 | Hendrickson et al. | 382/110 |
| 2009/0035782 A1 * | 2/2009 | Dillen et al. | 435/6 |
| 2009/0178159 A1 * | 7/2009 | Taramino et al. | 800/279 |
| 2009/0226042 A1 * | 9/2009 | Lejeune et al. | 382/110 |
| 2010/0042234 A1 * | 2/2010 | May et al. | 700/90 |
| 2012/0150341 A1 * | 6/2012 | Leyns et al. | 700/224 |

OTHER PUBLICATIONS

Lemnatec2008 Promotional Video, YouTube.com, www.youtube.com/watch?v=GvkTLugHAAw, uploaded and published online: Sep. 15, 2008, screen shots, part 1.†

(Continued)

*Primary Examiner* — Shervin Nakhjavan
(74) *Attorney, Agent, or Firm* — James E. Davis

(57) ABSTRACT

Automated systems and methods for screening individual plants for increased tolerance or sensitivity to various conditions are provided.

9 Claims, 4 Drawing Sheets

(56) References Cited

OTHER PUBLICATIONS

Lemnatec2008 Promotional Video, YouTube.com, www.youtube.com/watch?v=GvkTLugHAAw, uploaded and published online: Sep. 15, 2008, screen shots, part 2.†

Lemnatec2008 Promotional Video, YouTube.com, www.youtube.com/watch?v=GvkTLugHAAw, uploaded and published online: Sep. 15, 2008, transcript of audio.†

Norgren et. al., Non-destructive biomass estimation of tree seedlings using image analysis, Scand. J. for. Res. 10: 347-352 (1995), published on-line: Dec. 10, 2008.†

Mizoue et. al., Image analysis measure of crown condition, foliage biomass and stem growth relationships of *Chamaecyparis* obtuse. Forrest Ecology and Management, 172: 79-88, 2003, published Jan. 6, 2003.†

Ter-Mikaelian & Parker, Estimating biomass of white spruce seedlings with vertical photo imagery, New Forests 20: 145-162, published Sep. 2000.†

Varshney et al., "Genomics-assisted breeding for crop improvement" TRENDS in Plant Science, vol. 10 No. 12, published Dec. 2005.†

Presentation by Bob Furbank, of the Australian Plant Phenomics Facility, Canberra, Australia at the European Plant Science Organisation, EPSO Workshop on Plant Phenotyping, published Nov. 2-3, 2009, Forschungszentrum Julich, Germany.†

Lenk, et al., Multispectral fluorescence and reflectance imaging at the leaf level and its possible applications, J. of Experimental Botany, vol. 58, No. 4, pp. 807-814, 2007, advanced access and published Sep. 21, 2006.†

Blackburn, Hyperspectral remote sensing of pigments, J. of Experimental Botany, vol. 58, No. 4, pp. 855-867, advance access and published on Sep. 21, 2006, Imaging Stress Responses in Plants Special Issue.†

\* cited by examiner
† cited by third party

APPARATUS AND METHODS FOR AUTOMATED PHENOTYPIC SCREENING OF PLANT GENOTYPES

CROSS REFERENCE TO RELATED APPLICATION

This application claims priority to U.S. Provisional Application Ser. No. 61/259,819 (filed Nov. 10, 2009), which is incorporated by reference herein in its entirety.

FIELD

The present disclosure relates to the field of biotechnology, more specifically to apparatus and methods for automated phenotypic screening of plants with different genotypes.

SUMMARY

The present disclosure generally provides automated systems and methods for screening individual plants for increased tolerance or sensitivity to various conditions.

In various embodiments, the present disclosure comprises methods to draw on the phenotypic appearance of a select group of plants grown under environmentally controlled conditions to screen and select a plurality of transgenic events for their phenotypes. Pluralities of plants comprising nursery and process control plants as well as transgenic events are sown in individual pots. These pots are placed into a pot shuttle, or carrier, for movement within an automated plant screening complex. The automated plant screening complex comprises automated plant movement equipment for moving and monitoring plants on a plant-by-plant basis. Additionally, the individual plants are exposed to a controlled environment, and automatically provided with controlled amounts of water and/or nutrients based upon one or more assay definitions.

In other embodiments, the disclosure comprises an automated method for phenotypic screening of a population of plants. The method comprises subjecting the population of plants to an induced stress in a controlled environment and periodically delivering individual plants from the population of plants in the controlled environment to an imaging station. At the imaging station, a first image of each plant is collected to determine the position of the plant in the imaging station, the plant is oriented within the imaging station based upon the first image, and at least one additional image of the plant is collected.

In other embodiments, the disclosure comprises an automated method for measuring the biomass of a plant. The method comprises obtaining at least one overhead image of the plant, determining the widest radial axis of the plant, rotating the plant such that the determined widest radial axis of the plant is oriented toward a biomass imaging device, and acquiring an image of the plant with the biomass imaging device. The method is further characterized in that the acquired image is parallel to the plane defined by the intersection of the determined widest radial axis of the plant and the longitudinal axis of the plant.

In other embodiments, the disclosure comprises an apparatus for screening one or more potted plants for an induced stress response. The apparatus comprises an automated plant screening complex comprising at least one automated plant weighing station, at least one automated plant imaging station, and at least one automated fertigation station. The apparatus further comprises an automated conveyor system that supports and transports one or more potted plants through the automated plant screening complex and a computer system that controls and directs the automated conveyor system and the automated plant screening complex. The computer system also collects and evaluates data acquired by the automated plant screening complex for analyzing the one or more potted plants being subjected to the induced stress. In a particular embodiment, the apparatus further comprises at least one automated imaging station that is operable to image the one or more potted plants in the visible or hyperspectral range.

In still other embodiments, the disclosure comprises an automated method for the high-throughput phenotyping of a plurality of plants. The method comprises growing a population of plants, which may comprise one or more transgenic events, in a controlled environment for a defined growing period. The population of plants are subjected to at least one induced stress during the growing period and analyzed to determine a growth profile for individual plants in the population. The growth profile comprises at least three measurable characteristics selected from the group consisting of canopy area, chlorophyll content, anthocyanin content, biomass, plant height, root mass, water content, yield, the amount of water applied during the growing period, and water use efficiency. In particular embodiments, the growth profile is determined by periodically weighing the individual plants at an automated weighing station during the growing period, and periodically imaging the individual plants at an automated imaging station during the growing period. After the growth profile is determined, individual plants can be selected from the population of plants based upon the determined growth profile.

Further areas of applicability of the present teachings will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

Corresponding reference numerals indicate corresponding parts throughout the several views of drawings.

DETAILED DESCRIPTION

Figure 1:
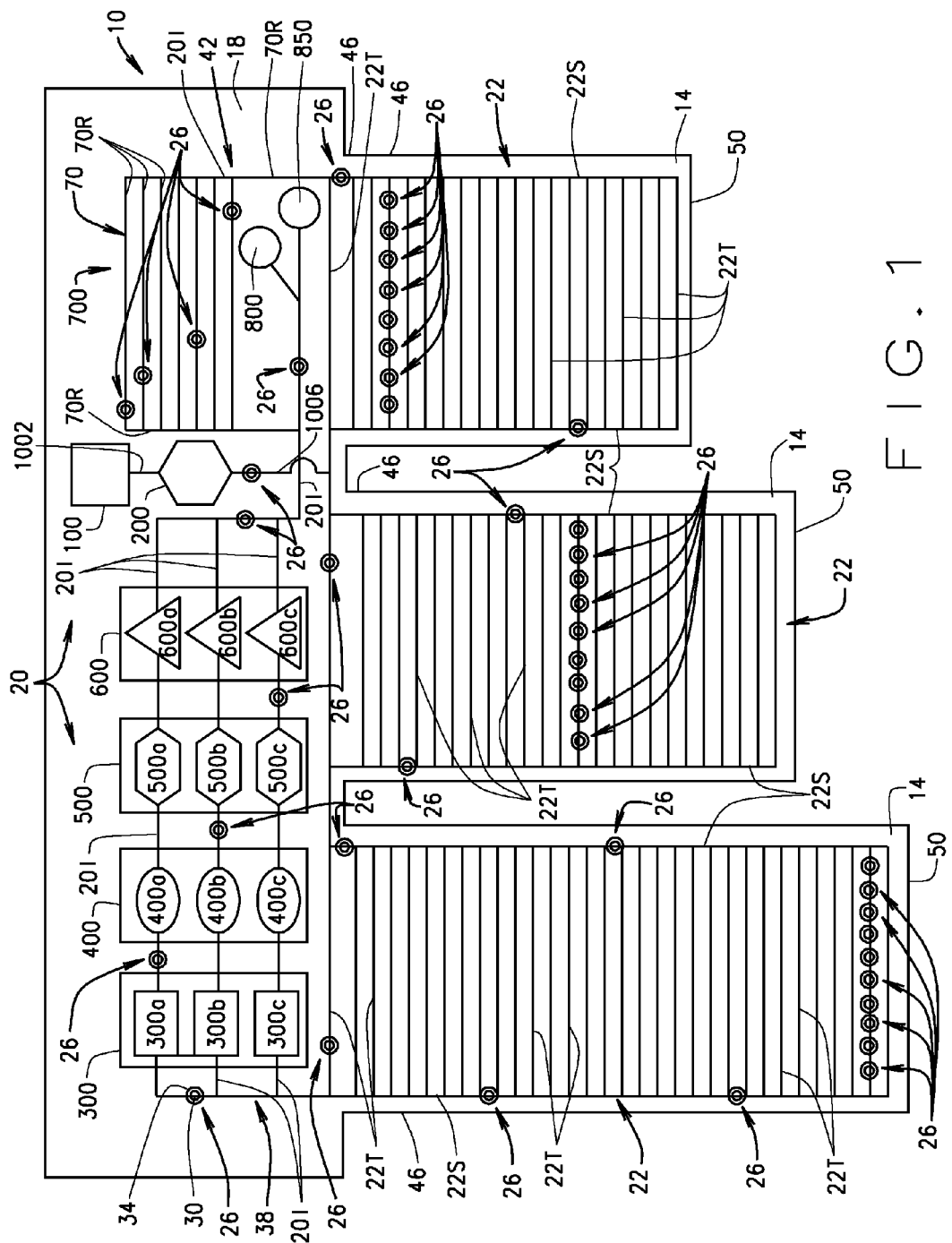
FIG. 1 is a block diagram of an automated plant screening complex, in accordance with various embodiments of the present disclosure.

The following description is merely exemplary in nature and is in no way intended to limit the present teachings, application, or uses. Throughout this specification, like reference numerals will be used to refer to like elements.

Generally, the present disclosure provides automated systems and methods for screening plants for increased tolerance or sensitivity to various stress conditions on a plant-by-plant basis.

As used herein the term "stress" means variation from optimal conditions to sub-optimal conditions of growth. Stress may be characterized as "biotic" stress or "abiotic" stress. "Biotic stress" is a stress on a plant caused by any factor that is itself alive such as plant pests. Plant pests include, but are not limited to arthropod pests, nematode pests, and fungal or microbial pests. "Abiotic stress" is a stress on a plant caused by one or more non-living chemical and physical factors in the environment such as light, temperature, water, atmospheric gases, wind as well as soil, and physiographic factors. Abiotic stresses useful for applying to plants being screened for genotypes that provide enhanced traits include water deficit stress, nitrogen deficit stress, cold stress, heat stress, sunlight stress (e.g. from shade), and the like.

As used herein, "genotype" describes the genetic constitution of an individual plant; distinct genotypes can be defined by the specific allelic makeup of individual plants or by unique transgenes in an otherwise common genotype.

As used herein, "grow" and "grown" describe the cultivation of plants to a desired stage, for example, grown to harvest or an earlier maturity state.

As used herein, "statistically randomized" means the assignation of a random position. That is, an assigned position or site in an array occupied or designated for occupancy by a seed or progeny plant without definite aim, direction, rule or method for the selection of the position.

A dicot plant is a member of a group of flowering plants whose seed typically contains two embryonic leaves or cotyledons. A monocot plant is a member of a group of flowering plants having one embryonic leaf. Crop plants are plants that are commonly cultivated. The screening of crop plants is a useful application of the methods of the present disclosure. Monocot crop plants include, but are not limited to, wheat, corn (maize), rice; and dicot crop plants include tomato, potato, soybean, cotton, canola, sunflower and alfalfa.

"Trait" refers to a plant phenotype and is generally observable from an interaction between the genotype of the plant and the environment. A trait can be observed by the naked eye or by any other means of evaluation known in the art, for example microscopy, biochemical analysis, imaging in the visible range, imaging in the hyperspectral range, imaging by x-ray or magnetic resonance, etc. At least one "measurable characteristic" is used to quantitatively describe a specific trait. Such measurable characteristics can be, but are not limited to plant height, plant width, canopy area, image-derived plant biomass, image-derived plant growth rate, plant morphology, plant weight, total plant or plant part dry matter weight, plant color, chlorophyll content, anthocyanin content, water content, water use efficiency, leaf number, leaf angle, germination rate, root mass, yield, leaf extension rate, chlorophyll level, ear length, ear diameter, ear tip void percentage, kernels per ear, average mass per kernel, total each shell weight, boll count, seed cotton weight, fruit and seed size, harvest moisture, husk length, stand count at harvest time in a unit area or per plot, metabolite quality and quantity which include oil, protein, carbohydrate or any other plant metabolite, food or feed content and value, and the like.

The apparatus and methods of the present disclosure can be used to determine one or more of the above measurable characteristics to screen plants for one or more quantitative or qualitative traits. In some embodiments, plants can be screened and/or selected for traits such as enhanced yield, enhanced resistance to an abiotic stress or enhanced yield by enhanced resistance to an abiotic stress. In other embodiments, the plants can be screened and/or selected for traits such as resistance or tolerance to an herbicide. In other embodiments, the plants can be screened and/or selected for an enhanced trait such as resistance to a biotic stress such as enhanced resistance to soybean cyst nematode or corn rootworm, or boll weevil, or a virus or fungus. In other embodiments the plants can be screened and/or selected for an enhanced trait such as root lodging, stalk lodging, plant lodging, plant height, plant morphology, ear development, tassel development, plant weight, plant maturity, total plant or plant part dry matter, fruit and seed size, harvest moisture, husk length, stand count at harvest time in a unit area or per plot, metabolite quality or content which include oil, protein, carbohydrate or any other plant metabolite, food or feed content and value, physical appearance, male sterility, and the like.

As those skilled in the art will readily recognize, the present disclosure can be practiced to screen plants using any combination of phenotypic traits that can be imparted by different genotypes or, more specifically imparted by one or more transcribable polynucleotides introduced into plants such as a gene of agronomic interest.

As used herein, the term "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. Suitable transcribable polynucleotide molecules include but are not limited to those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, or an insecticidal protein.

The expression of a gene of agronomic interest is often desirable in order to confer an agronomically important trait. Non-limiting examples of genes of agronomic interest that provide a beneficial agronomic trait to crop plants can include genetic elements comprising herbicide resistance (as described, for example, in U.S. Pat. Nos. 6,803,501; 6,448,476; 6,248,876; 6,225,114; 6,107,549; 5,866,775; 5,804,425; 5,633,435; and 5,463,175, all of which are incorporated herein by reference), increased yield (as described, for example, in U.S. Pat. Nos. RE38,446; 6,716,474; 6,663,906; 6,476,295; 6,441,277; 6,423,828; 6,399,330; 6,372,211; 6,235,971; 6,222,098; and 5,716,837, all of which are incorporated herein by reference), insect control (as described, for example, in U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; and 5,763,241, all of which are incorporated herein by reference), fungal disease resistance (as described, for example, in U.S. Pat. Nos. 6,653,280; 6,573,361; 6,506,962; 6,316,407; 6,215,048; 5,516,671; 5,773,696; 6,121,436; 6,316,407; and 6,506,962, all of which are incorporated herein by reference), virus resistance (as described, for example, in U.S. Pat. Nos. 6,617,496; 6,608,241; 6,015,940; 6,013,864; 5,850,023; and 5,304,730, all of which are incorporated herein by reference), nematode resistance (as described, for example, in U.S. Pat. No. 6,228,992, which is incorporated herein by reference), bacterial disease resistance (as described, for example, in U.S. Pat. No. 5,516,671, which is incorporated herein by reference), plant growth and development (as described, for example, in U.S. Pat. Nos. 6,723,897 and 6,518,488, all of which are incorporated herein by reference), starch production (as described, for example, in U.S. Pat. Nos. 6,538,181; 6,538,179; 6,538,178; 5,750, 876; and 6,476,295, all of which are incorporated herein by reference), modified oils production (as described, for example, in U.S. Pat. Nos. 6,444,876; 6,426,447; and 6,380, 462, all of which are incorporated herein by reference), high oil production (as described, for example, in U.S. Pat. Nos. 6,495,739; 5,608,149; 6,483,008; and 6,476,295, all of which are incorporated herein by reference), modified fatty acid content (as described, for example, in U.S. Pat. Nos. 6,828, 475; 6,822,141; 6,770,465; 6,706,950; 6,660,849; 6,596,538; 6,589,767; 6,537,750; 6,489,461; and 6,459,018, all of which are incorporated herein by reference), high protein production (as described, for example, in U.S. Pat. No. 6,380,466, which is incorporated herein by reference), fruit ripening (as described, for example, in U.S. Pat. No. 5,512,466, which is incorporated herein by reference), enhanced animal and human nutrition (as described, for example, in U.S. Pat. Nos. 6,723,837; 6,653,530; 6,5412,59; 5,985,605; and 6,171,640, all of which are incorporated herein by reference), biopolymers (as described, for example, in U.S. Pat. Nos. RE37,543; 6,228,623; and 5,958,745 and U.S. Patent Publication No. US20030028917, all of which are incorporated herein by reference), environmental stress resistance (as described, for example, in U.S. Pat. No. 6,072,103, which is incorporated herein by reference), pharmaceutical peptides and secretable peptides (as described, for example, in U.S. Pat. Nos. 6,812, 379; 6,774,283; 6,140,075; and 6,080,560, all of which are incorporated herein by reference), improved processing traits (as described, for example, in U.S. Pat. No. 6,476,295, which is incorporated herein by reference), improved digestibility (as described, for example, in U.S. Pat. No. 6,531,648, which is incorporated herein by reference), low raffinose (as described, for example, in U.S. Pat. No. 6,166,292, which is incorporated herein by reference), industrial enzyme production (as described, for example, in U.S. Pat. No. 5,543,576, which is incorporated herein by reference), improved flavor (as described, for example, in U.S. Pat. No. 6,011,199, which is incorporated herein by reference), nitrogen fixation (as described, for example, in U.S. Pat. No. 5,229,114, which is incorporated herein by reference), hybrid seed production (as described, for example, in U.S. Pat. No. 5,689,041, which is incorporated herein by reference), fiber production (as described, for example, in U.S. Pat. Nos. 6,576,818; 6,271, 443; 5,981,834; and 5,869,720, all of which are incorporated herein by reference) and biofuel production (as described, for example, in U.S. Pat. No. 5,998,700, which is incorporated herein by reference). The genetic elements, methods, and transgenes described in the patents listed above are incorporated herein by reference.

Alternatively, a transcribable polynucleotide molecule can effect the above mentioned plant characteristic or phenotype by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any transcribable polynucleotide molecule that encodes a transcribed RNA molecule that affects a phenotype or morphology change of interest can be useful for the practice of the present disclosure.

In various embodiments, the methods of the present disclosure are practiced on a plant population that is exposed to a controlled environment. A controlled environment facilitates the screening of a population of plants in a set or subset of plants with an enhanced desired trait. For example, drought tolerant plants within a population are identified by exposing the plant population to drought. Similarly, herbicide tolerant plants within a population are identified by exposing the plant population to a specific herbicide, while insect tolerant plants within a population are identified by exposing the plant population to a specific insect. As further examples, nitrogen deficit tolerant plants within a population are identified by exposing the plant population to a nitrogen deficit. And, plants with enhanced yield within a population are identified by measuring one or more yield characteristics such as plant height at various time points, growth rate (i.e., change over a period of time), chlorophyll fluorescence, anthocyanin content, differential light reflectrometry (Normalized difference vegetative index, NDVI) or transmission spectrometry (SPAD) or actual grain yield by harvesting from individual plants.

In various embodiments, automated phenotypic screening of plants, utilizing the presently disclosed systems and methods, employs standard statistical analysis methods (which include experimental blocking and spatial autocorrelation and trend analysis) thereby, allowing infinitely large experiments to be planted and screened. These experiments enable easy and rapid tests of tens of thousands of genetic variants simultaneously in a single experiment.

As used herein, the term "transgenic" refers to an animal, plant, or other organism containing one or more heterologous nucleic acid sequences.

As used herein, a "transgenic plant" is a plant whose genome has been altered by the stable integration of recombinant DNA. A transgenic plant can include a plant regenerated from an originally-transformed plant cell and progeny transgenic plants from later generations or crosses of a transformed plant.

The term "non transgenic plant", as used herein, is a plant whose genome has not been altered by stable integration of recombinant DNA. Non transgenic plants include natural plants and plants varieties that are created without using recombinant DNA technology.

As used herein, "control plant" means a plant that does not comprise a genotype being screened for a trait, e.g. a plant that does not comprise the recombinant DNA or mutant DNA.

Including a number of control plants in a population provides a baseline for screening. A suitable control plant can be a non-transgenic plant of the parental line used to generate a transgenic plant, i.e. devoid of recombinant DNA. Alternatively, a suitable control plant can in some cases be a progeny of a hemizygous transgenic plant line that does not comprise the recombinant DNA, known as a negative segregant.

A negative control plant is one that exhibits a deleterious phenotype when exposed to conditions in an assay for one or more measurable characteristics. A positive control plant is one that exhibits a beneficial phenotype when exposed to conditions in an assay for one or more measurable characteristics.

The term "transformation", as used herein, refers to the introduction of nucleic acid into a recipient host.

The term "host", as used herein, refers to bacteria cells, fungi, animals and animal cells, plants and plant cells, or any plant parts or tissues including protoplasts, calli, roots, tubers, seeds, stems, leaves, seedlings, embryos, and pollen.

As used herein, the term "transformed" refers to a cell, tissue, organ, or organism into which has been introduced a foreign polynucleotide molecule, such as a construct. The introduced polynucleotide molecule can be integrated into the genomic DNA of the recipient cell, tissue, organ, or organism such that the introduced polynucleotide molecule is inherited by subsequent progeny.

A "transgenic" or "transformed" cell or organism can also include progeny of the cell or organism and progeny produced from a breeding program employing such a transgenic plant as a parent in a cross and exhibiting an altered phenotype resulting from the presence of a foreign polynucleotide molecule.

Referring now to FIG. 1, as set forth above, in various embodiments, the present disclosure provides systems and methods for screening, i.e., testing, observing, collecting and analyzing data for, plant populations for one or more measurable characteristics or particular phenotypic traits. More particularly, various plant assays are conducted on plant populations exposed to controlled environments or controlled growth conditions, e.g., controlled climate, hydration and nutrition, within an automated plant screening complex 10 that is structured and operable to automatically screen each plant in each of the various assays and/or populations to identify plants that possess one or more measurable characteristics or particular phenotypic traits. Subsequently, plant lines with genetic variation conferring better performance can be identified and advanced to further testing, while plant lines with genetic variation conferring deleterious impacts on plant performance can be identified and removed from further study.

Generally, the screening complex 10 is a climate controlled structure, or plurality of connected structures, that includes a plurality of automated systems and subsystems. The automated systems and subsystems are structured and operable to provide, inter alia, automated pot filling, automated sowing of seed, automated periodic weighing, automated periodic imaging, automated periodic fertigation and automated movement and re-ordering of plants within the screening complex 10. The periodic weighing, imaging and fertigation can be performed at any desired scheduled period, for example daily, every two days, every three days, once a week, etc., or some combination thereof.

In various embodiments, the screening complex 10 includes one or more greenhouses 14 that are connected to a headhouse 18. In operation, plants are moved, via an automated conveyor system, between the one or more greenhouses 14, where the plants are cultivated in a climate controlled environment, and the headhouse 18 where the plants are weighed, fertigated and imaged in accordance with a selected testing protocol. For example, in various embodiments, the screening complex 10 is operable to collect and track periodic physiological measurements of each plant, including weight, biomass, image data, plant-specific watering/fertigation data, and the like, as each plant is transported from the greenhouse(s) 14 to the headhouse 18. The collected data can be used to provide rate-based metrics used to identify measurable characteristics or traits useful in any of a variety of assays such as nitrogen use efficiency (NUE), water use efficiency (WUE) and/or non-stress, i.e., yield, conditions for selected plants.

The headhouse 18 houses an instrumentation line 20 that, in various embodiments, includes a potting station 100, a seed sowing station 200, a weighing station 300, an orientation station 400, an imaging station 500, a fertigation station 600, a re-order station 700, and a discard station 800. Additionally, the one or more greenhouses 14 includes a plurality of plant movement subsystems 22 that are structured and operable to automatically move a plurality of test units 26 between the greenhouse(s) 14 and the headhouse 18 throughout the screening process, as described below.

The potting station 100 is structured and operable to fill each of a plurality of pots 30 with a predetermined amount of planting media. Particularly, in various embodiments, the potting station 100 can include a pot filling machine (not shown) that is structured and operable to automatically meter out a predetermined amount of planting media and automatically fill each pot 30 with a metered amount of planting media. The pot filling machine can be any machine, apparatus or system structured and operable to measure the planting media and deposit the media in the pots 30, such as that commercially available from AgriNomix, located in Oberlin, Ohio. Additionally, in various embodiments, the potting station 100 can be structured and operable to place each filled pot 30 on an automated conveyor 1002 that automatically moves each filled pot 30 from the potting station 100 to the seed sowing station 200. The planting media can be any planting media suitable to meet the parameters of a given screening protocol. For example, the planting media can comprise various soil mixtures, various soil-less mixtures, or any combination thereof.

Alternatively, in various embodiments, the potting station 100 can be structured and operable to assist a person in metering out the predetermined amount of planting media and depositing the metered planting media in the pots 30, i.e., provide the tools, devices, mechanisms, etc., for the person to measure the planting media and deposit the media in the pots 30. In such embodiments, the person can place the filled pots 30 on the automated conveyor 1002, or alternatively, manually deliver the filled pots to the seed sowing station 200.

The seed sowing station 200 may be structured and operable to perform one or more of the functions of sowing one or more selected seeds in each of the planting media filled pots 30, placing each pot 30 with the respective sown seed(s) into a corresponding pot shuttle, or carrier, 34, and logging data into a database that corresponds each sown seed to its respective pot shuttle 34 retaining the respective pot 30.

Particularly, to maintain the relationship between each sown seed with its respective pot shuttle 34, each pot shuttle 34 includes a shuttle identification tag disposed thereon. Each shuttle identification tag is linked, tied, correlated or associated with the seed sown in the respective pot 30 within a database accessible by a computer-based screening complex control system (not shown) that controls some or all the operations of the screening complex 10, as described herein. More particularly, each shuttle identification tag includes a unique identifier, i.e., information or data, that is unique to and identifies the respective pot shuttle 34. Additionally, each seed to be sown is preselected based on its respective characteristics or genotype.

Hence, at the time each seed is sown, the particular seed type is recorded/entered into the database, and then as the sown seed and respective pot 30 are placed in a pot shuttle 34, the unique identifier provided by the shuttle identification tag of the respective pot shuttle 34 is recorded/entered into the database. Accordingly, each sown seed is linked, tied, correlated or associated with the respective pot shuttle 34 that retains the sown seed and respective pot 30, such that various growth and health metrics of the resulting plant can be monitored and tracked throughout the screening process. Alternatively, the unique identifier provided by the shuttle identification tag of the respective pot shuttle 34 can be recorded/entered into the database first. Then, subsequently, the plant media filled pot 30 can be placed into the pot shuttle 34, the respective seed sown, and the particular seed type recorded/entered into the database to link, tie, correlate or associate the pot shuttle 34 with the respective sown seed.

Recording the particular seed type within the database can be achieved in any suitable manner. For example, in various embodiments, a packet containing a plurality of a selected seed type can include a seed type identification label, e.g., a barcode that includes a unique identifier, i.e., information or data, that is unique to and identifies the respective seed type. Accordingly, the seed type identification label on the packet can be read, e.g., scanned, prior to the respective seeds being sown. Alternatively, each seed type can be manually entered based on information provided by the seed type identification label. In various other embodiments, any suitable machine-readable seed type identification labels can be used, such as two-dimensional matrix codes or other machine-readable labels, tags or devices in which the data is received and interpreted via wireless communication such as optical signals, e.g., infrared signals, or magnetic fields.

Similarly, the shuttle identification tags can be any device or item suitable for providing unique identification information for each respective pot shuttle 34. For example, in various embodiments, each shuttle identification tag can comprise a radio frequency identification (RFID) tag having the unique identifier, i.e., information or data, electronically stored therein. In such instances, the unique identifier is receivable/readable by each of a plurality of suitable RFID receivers/readers located at various selected locations throughout the screening complex 10. In various other embodiments, any suitable machine-readable shuttle identification tags can be used, such as two-dimensional matrix codes or other machine-readable tags or devices in which the data is received and interpreted via wireless communication such as optical signals, e.g., infrared signals, or magnetic fields.

Thus, in a particular embodiment, the sowing station 200 is structured and operable to receive each plant media filled pot 30 from the potting station 100, sow at least one selected seed type into each pot 30, place the sown seed and pot 30 into a pot shuttle 34, and link each pot shuttle 34 with the respective seed type within the database.

As used herein, each test unit 26 comprises a pot shuttle 34 having a corresponding pot 30 filled with the planting media and sown seed(s) (or resulting plant(s)) retained therein. Thus, the sowing station 200 outputs completed test units 26, wherein each test unit 26 includes at least one seed having a particular selected genotype or characteristics sown within a plant media filled pot 30 that is retained within a respective pot shuttle 34, wherein each pot shuttle 34 is uniquely identified and linked with the respective seed(s), and more particularly, with the selected genotype/characteristics of the respective seed(s).

In various embodiments, in addition to each test unit 26 having the respective sown seed(s) and pot shuttle 34 linked within the database, each test unit 26 is selectively assigned to one or more particular assay definition template within the database. Each assay definition template is designed to implement one of a plurality of screening protocols designed to screen plants for increased tolerance or sensitivity to various selected environmental or stress conditions, e.g., water, light, temperature, humidity, and nutrients.

For example, various selected seeds/plants may be assigned to a particular assay definition template designed to implement a water use efficiency (WUE) screening protocol to screen for increased tolerance to water deficiency, wherein the particular assay definition template stipulates the climate (i.e., temperature, light and humidity), daily amounts of water and daily amounts and type of nutrients each seed/plant will be subjected to during the life cycle of the respective water deficiency screening. Similarly, various other selected seeds/plants may be assigned to a particular assay definition template designed to implement a nitrogen use efficiency (NUE) screening protocol to screen for increased tolerance to nutrient deficiency, wherein the particular assay definition template stipulates the climate, daily amounts of water and daily amounts and type of nutrients each seed/plant will be subjected to during the life cycle of the respective nutrient deficiency screening.

Still yet, various other selected seeds/plants may be assigned to a particular assay definition template designed to implement a yield screening protocol, wherein the particular assay definition template stipulates the climate, daily amounts of water and daily amounts and type of nutrients each seed/plant will be subjected to during the life cycle of screening. Still further, various other selected seeds/plants may be assigned to a particular assay definition template designed to implement a temperature and/or light sensitivity protocol, wherein the particular assay definition template stipulates the climate, daily amounts of water and daily amounts and type of nutrients each seed/plant will be subjected to during the life cycle of the respective temperature and/or light sensitivity screening.

It should be understood that a plurality of such WUE, NUE, temperature, light sensitivity, etc., screening protocols can be implemented substantially simultaneously within the same, or different, greenhouses 14. It should also be understood that each screening protocol can be implemented using a variety of different assay definition templates. That is, various assay definition templates can be employed to implement different degrees, types or severities of any given screening protocol. For example, a plurality of assay definition templates can be designed to stipulate different climates, daily amounts of water and daily amounts and type(s) of nutrients each seed/plant will be subjected in order to implement various degrees, types, or severity of water deficiency screening. More specifically, each assay definition template would be designed to implement a WUE screening of a different degree, type, or severity.

Each assay definition template is implemented by the screening complex control system to control the climate maintained within each greenhouse 14 and the operations of the fertigation station 600 in order to subject each seed/plant to the particular selected conditions, e.g., water, light, temperature, humidity, and nutrients, during the screening in accordance with the respective assay definition template.

Once each sown seed is linked to the respective pot shuttle 34 and each test unit 26 is assigned a particular assay definition template within the database, each test unit 26 is conveyed to a particular greenhouse 14 and/or to a particular section of the respective greenhouse 14, via a conveyor 1006. More specifically, via the conveyor 1006, each test unit 26 is conveyed from the sowing station 200 to the respective plant movement subsystem 22. Each plant movement subsystem 22 includes a pair of side conveyors 22S and a plurality of transverse conveyors 22T disposed substantially orthogonally between the respective side conveyors 22S. The side and transverse conveyors 22S and 22T are structured and operable to convey each of the test units 26 from the respective greenhouse 14 to a head 38 of the instrumentation line 20, and from an end 42 of the instrumentation line 20 back to the respective greenhouse 14, as controlled by the screening complex control system. As described below, each of the test units 26 are conveyed between the head 38 and the end 42 of the instrumentation line 20 and to each of the stations 300, 400, 500, 600 and 700 located therebetween, via a plurality of instrumentation line conveyors 20I, as controlled by the screening complex control system.

In various embodiments, the spacing between the transverse conveyors 22T can be varied to allow for adequate spacing between the plants as the plants grow throughout the respective screening. For example, in various embodiments, the transverse conveyors 22T closer to a proximal end 46 of the respective greenhouse 14 can be spaced further apart than the transverse conveyors 22T near a distal end 50 of the respective greenhouse 14 to allow for increased plant width as the plants grow. Thus, as described below, during the duration of the respective screening, the position/location of each plant within the respective greenhouse 14 will transition from the transverse conveyors 22T near greenhouse distal end 50 to the transverse conveyors 22T near the greenhouse proximal end 46.

As used herein, the screening complex control system can be a single computer based system, or a plurality of computer based subsystems networked together to coordinate the simultaneous operations of the screening complex 10, described herein. For example, the screening complex control system can include a plurality of controller subsystems, e.g., a controller subsystem for each station 300, 400, 500, 600, 700 and 800 described herein. In such instances, each controller subsystem can include one or more processors or microprocessors that communicate with various station sensors, devices, mechanisms, motors, tools, etc., used in operation of the respective station 300, 400, 500, 600, 700 and 800. Each such controller subsystem can be networked together with a main computer to cooperatively operate all the stations, systems and subsystems of the screening complex 10, as described herein. Or alternatively, the screening complex control system can comprise a single computer communicatively connected to all the various sensors, devices, mechanisms, motors, tools, etc., to cooperatively operate all the stations, systems and subsystems of the screening complex 10, as described herein. For simplicity and clarity all computer based operations, functions, calculations and instructions will be described herein as being carried out by the screening complex control system although, as described above, each respective station 300, 400, 500, 600, 700 and 800 could include a computer based subsystem operable to carry out some or all of the operations, functions, calculations and instructions described herein with respect to the respective station.

Figure 2:
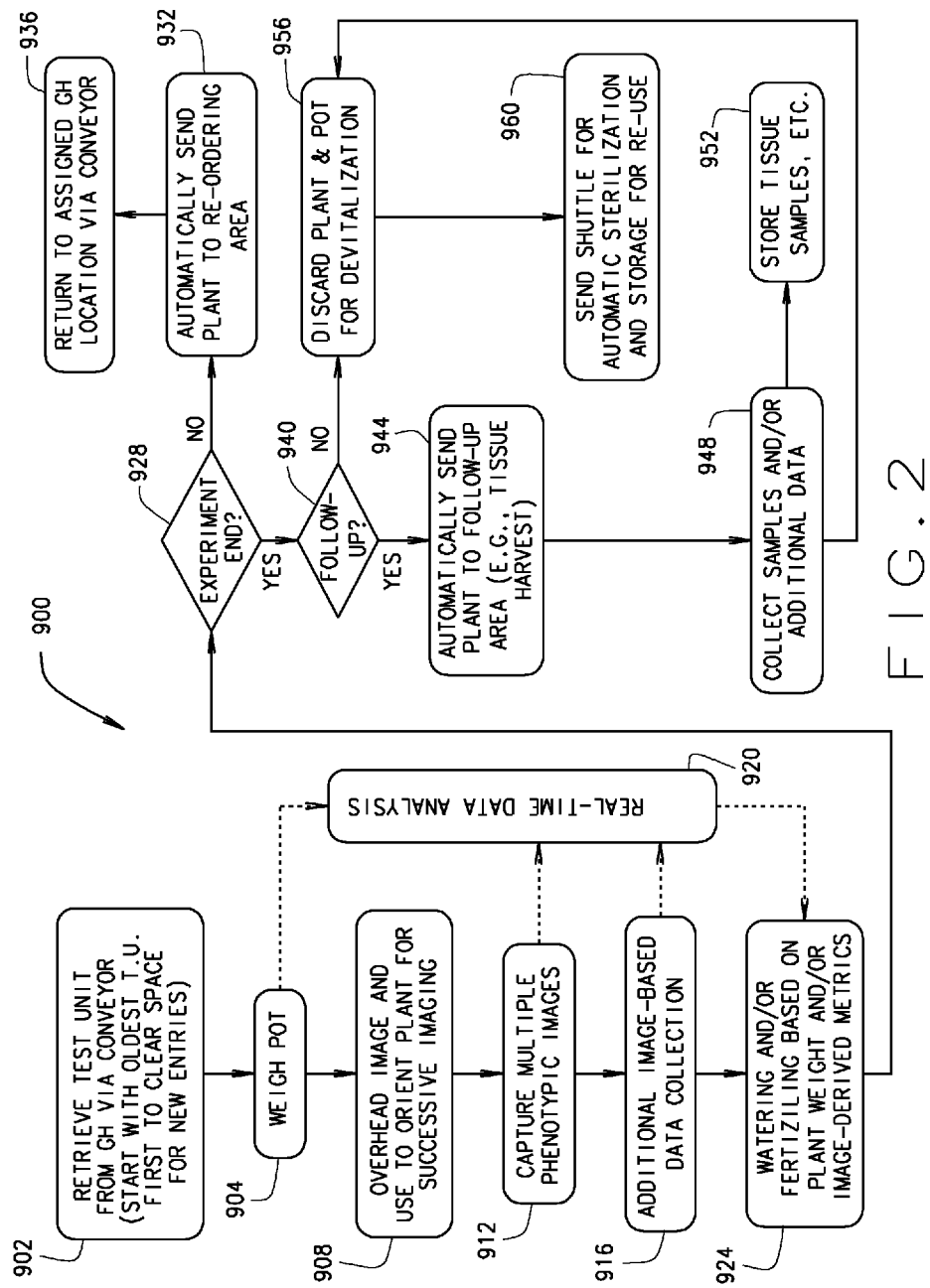
FIG. 2 is a flow chart illustrating various operations of the automated plant screening complex shown in FIG. 1, in accordance with various embodiments of the present disclosure.
Figure 3:
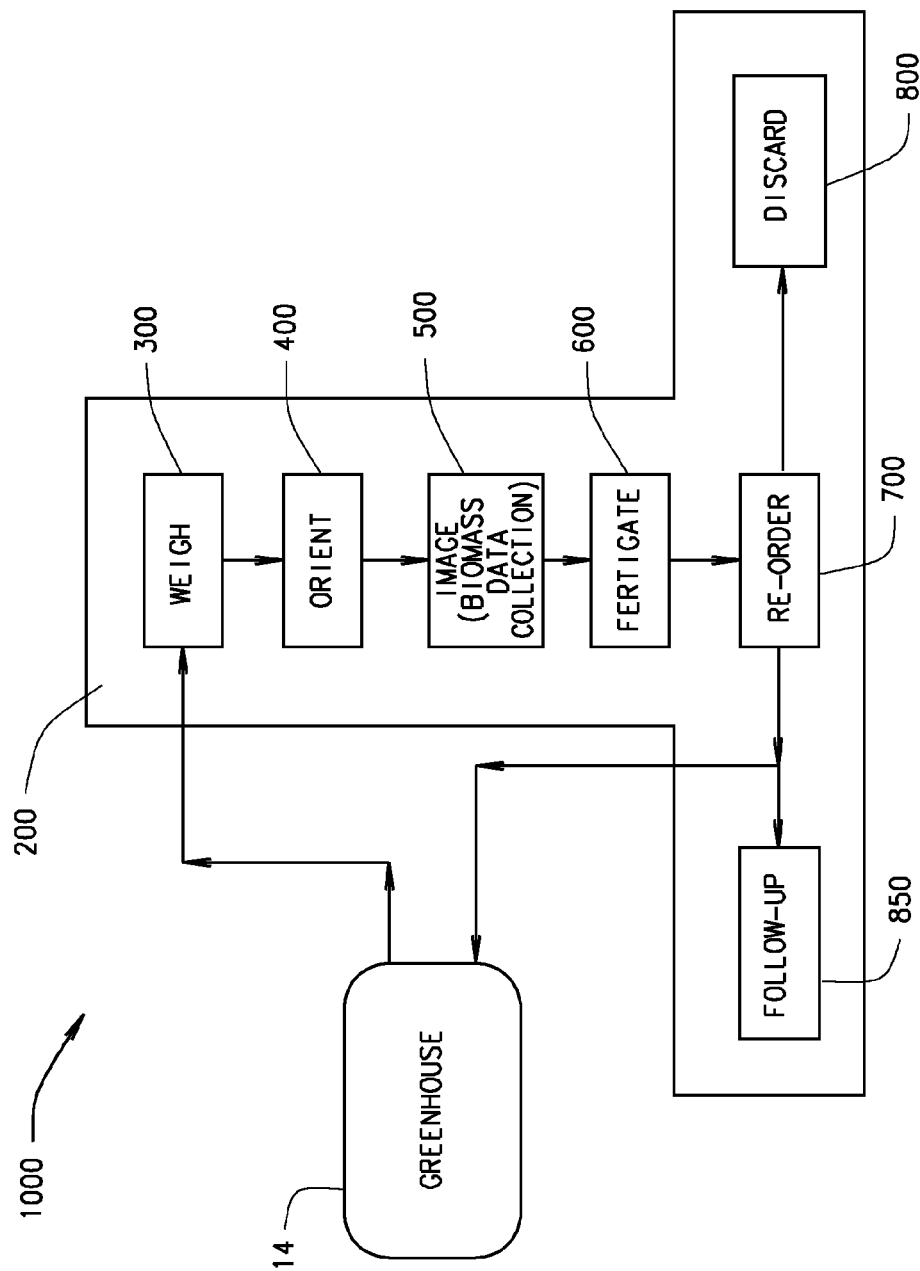
FIG. 3 is a sequence chart illustrating an exemplary sequence of conveyance for each of a plurality of test units being screened during operation of the automated plant screening complex shown in FIG. 1, in accordance with various embodiments of the present disclosure.

Referring now to FIGS. 1, 2 and 3, as described above, the automated screening complex 10 is operated such that each of the seeds/plants may be processed through the instrumentation line 20 at various times where each seed/plant is weighed, imaged and/or watered/fertilized to maintain appropriate nutrient or stress levels as specified in the respective assay definition template. Throughout the screening process, data is collected to enable the identification of particular plants that are significantly outperforming matched control seeds/plants in response to the imparted growth conditions. Such data can include, but is not limited to plant height, plant width, canopy area, stem diameter, image-derived plant biomass, image-derived plant growth rate, plant color, chlorophyll content, anthocyanin content, water content, leaf number, leaf angle, leaf tip burn, root mass, internode length (i.e., distance between leafs), the amount of water applied during the assay, and water use efficiency.

As also described above, once each sown seed has been linked to the respective pot shuttle 34 and each test unit 26 has been assigned a particular assay definition template within the database, each test unit 26 is conveyed to a particular greenhouse 14 and/or to a particular section of the respective greenhouse 14. In various embodiments, each test unit 26 is conveyed from the sowing station 200 to an initial position/location on one of the greenhouse transverse conveyors 22T near the distal end 50 of the respective greenhouse 14. From this initial position each test unit 26, i.e., each respective seed/plant, is conveyed to the instrumentation line 20 and back in accordance with a schedule stipulated in the particular assay definition template assigned to each respective test unit 26, e.g., daily, every two days, every three days, once a week, etc., or some combination thereof.

FIG. 2 provides a flow chart 900 illustrating an exemplary screening life cycle of an assay of test units 26 as executed via operation of the screening complex 10. FIG. 3 provides a sequence chart 1000 illustrating an exemplary sequence of conveyance for each test unit 26 being screened during operation of the screening complex 10. On each scheduled screening day stipulated by the respective assay definition template, e.g., daily, every other day, weekly, etc., each of the test units 26 in the assay are conveyed from the respective greenhouse 14 to the head 38 of the instrumentation line 20, as indicated at 902. As described above, conveyance of the test units 26 from the greenhouse 14 to the instrumentation line 20 is accomplished via cooperative operation of the greenhouse side and transverse conveyors 22S and 22T as controlled by the screening complex control system. In various embodiments, if more than one assay is to be screened on a particular day, the test units 26 within that are closest to the proximal end 46 of the greenhouse 14, i.e., the test units 26 nearing the end of their respective screening life cycle are conveyed to the instrumentation line head 38 first.

As illustrated in FIG. 2, in various embodiments, the instrumentation line 20 can include a plurality of processing lines to expedite the screening of the test unit 26. That is, each station 300, 400, 500 and 600 can include a plurality of substations, e.g., substations 'a', 'b', 'c', etc., that comprise the respective stations 300, 400, 500 and 600. Hence, a first processing line can include a weighing substation 300a, an orientation substation 400a, an imaging substation 500a and a fertigation substation 600a. Similarly, a second processing line can include a weighing substation 300b, an orientation substation 400b, an imaging substation 500b and a fertigation substation 600b, and so on. However, for simplicity and clarity each test unit 26 will be described herein as being processed through the weighing station 300, the orientation station 400, the imaging station 500 and the fertigation station 600 of the instrumentation line 20.

Upon each test unit 26 being conveyed to the instrumentation line head 38, each test unit 26 is subsequently conveyed to the weighing station 300 where each test unit 26 is weighed, as indicated at 904. The weighing station 300 can include any weight measurement device or scale and associated system(s) suitable for weighing each test unit 26 to acquire weight data that is subsequently communicated to the screening complex control system. For example, in various embodiments, the weighing station 300 can comprise an in-line scale that is included in the instrumentation line conveyor 20I so that the test units 26 do not need to be removed from the instrumentation line conveyor 20I to be weighed. The weighing station 300 additionally includes a shuttle identification tag reader, e.g., an RFID reader, for reading the shuttle identification tag disposed on the shuttle of each test unit 26 being weighed, and a data communication device, e.g., a wireless transmitter, structured and operable to communicate the weight and unique identifier stored in the respective shuttle identification tag, to the screening complex control system. In various embodiments, the shuttle identification tag reader can comprise the data communication device.

Subsequently, based on the measured weight, the screening complex control system will calculate the weight gain or loss of each respective test unit 26, and hence, the respective plant. The weight gain or loss is calculated with respect to a particular prior weight measurement as stipulated in the particular assay definition template assigned to the respective test unit 26. For example, the screening complex control system can calculate the weight gain/loss over the previous twenty-four hours, the previous two days, the previous week, the current life of the screening, etc., or some combination thereof. The measured weight and/or the calculated weight gain/loss is stored in the database and used independently or in aggregate with data collected at the imaging station 500, described below, to calculate an amount of water and/or nutrients the respective plant is to receive in accordance with the screening protocol and associated assay definition template.

After each test unit 26 is weighed at the weighing station 300, each test unit 26 is conveyed to the orientation station 400, via the instrument line conveyors 20I, where the pot 30 and respective plant of each test unit 26 is rotated, if necessary, to have a particular desired orientation for conveyance to the imaging station 500, as indicated at 908. That is, the orientation station 400 is structured and operable to rotate each pot 30 within the respective pot shuttle 34 of each respective test unit 26 such that the respective plant is oriented, i.e., positioned, to provide one or more desired imaging angles for phenotypic image data collection at the imaging station 500, as described below.

More specifically, because plants are neither cylindrical nor perfectly symmetrical, the orientation of the plant relative to an imaging device for collecting phenotypic image data can significantly affect biomass estimates generated utilizing the collected phenotypic image data, as is performed at the imaging station 500 described below. Thus, Applicants have discovered that placing plants such that the major horizontal axis, i.e., the substantially horizontal axis of the plant at the point where the plant is the widest, is at a consistent angle to the imaging device reduces this variability and significantly improves the quality of the collected image data and resulting biomass measurement.

Hence, the orientation station 400 includes an orientation imaging device, e.g., a digital, infrared or magnetic imaging device, that is structured and operable to acquire an overhead image of each plant as the respective test unit 26 remains on the instrument line conveyor 20I. Additionally, the orientation station 400 includes an orientation device structured and operable to rotate the pot 30 and respective plant within the pot shuttle 34 such that the major horizontal axis of each respective plant will be substantially orthogonal to an incident angle of a primary biomass imaging device of the imaging station 500 upon conveyance of the respective test unit 26 to the imaging station 500.

In various embodiments, upon arrival of each test unit 26 at the orientation station 400, the orientation imaging device acquires an overhead, or top view, image of the respective plant. Image analysis software executed by the screening complex control system computes the major horizontal axis of the plant and the angle, or amount, of rotation required to orient the respective plant such that the major horizontal axis of each respective plant will be substantially orthogonal to an incident angle of a primary biomass imaging device of the imaging station 500. The orientation device of the orientation station 400 then rotates the pot 30 and respective plant the computed amount of rotation within the pot shuttle 34. The orientation device can be any device, apparatus or system suitable for rotating each pot 30 such that the pot 30 and respective plant are properly oriented, as described above, within the pot shuttle 34. For example, in various embodiments, the orientation device can be structured and operable to lift each pot 30 from the respective pot shuttle 34, turn each pot 30 the computed amount, e.g., the computed number of degrees, and lower each pot 30 back into the respective pot shuttle 34.

After the pot 30 and respective plant is properly oriented within the respective pot shuttle 34, each test unit 26 is conveyed to the imaging station 500, via the instrument line conveyors 20I, where image data of each plant, e.g., digital or other visible light image data, hyper-spectral image data, multi-spectral image data, electromagnetic image data, and/or X-ray image data, is collected, as indicated at 912 and 916.

Figure 4:
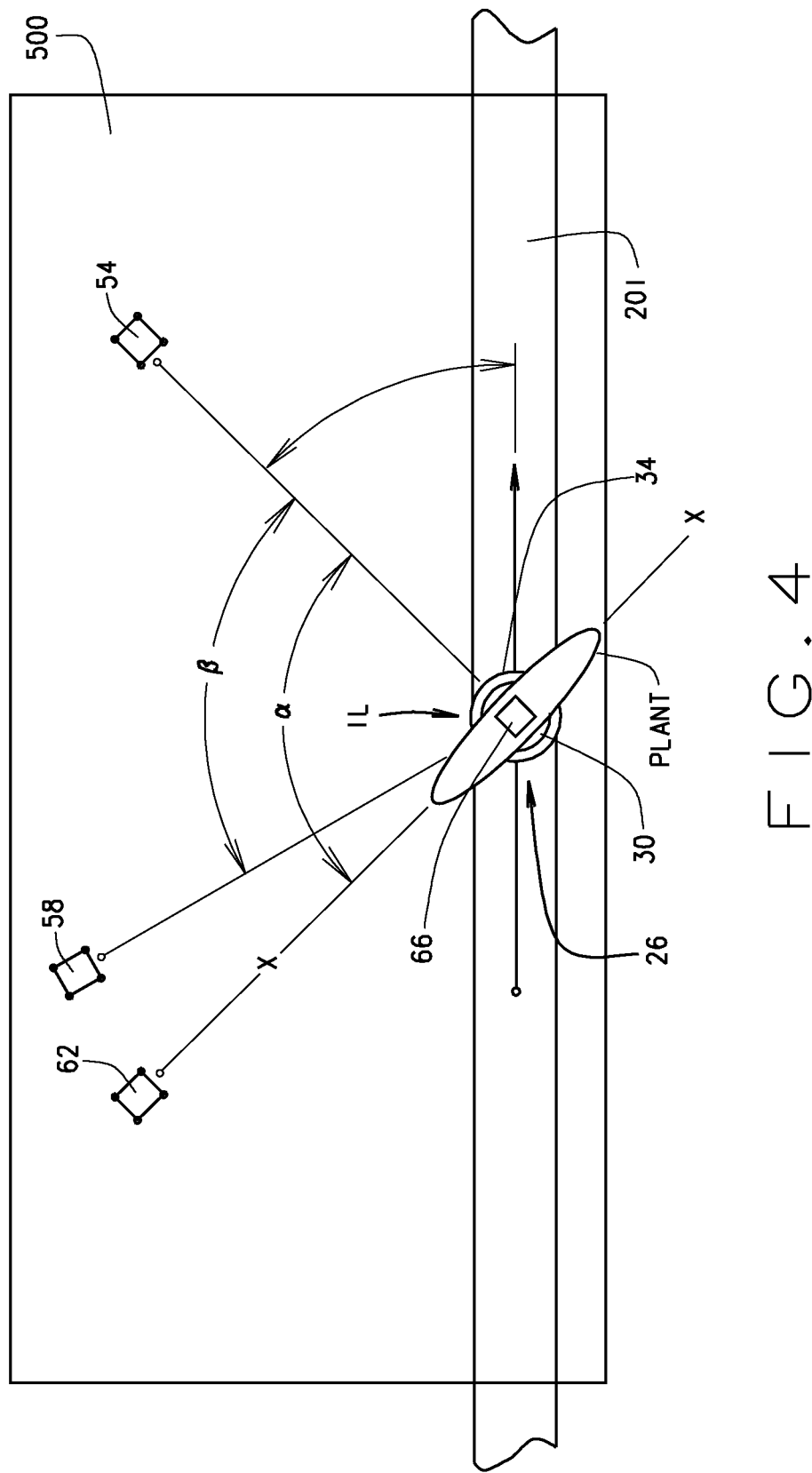
FIG. 4 is a general schematic top view of an imaging station of the automated plant screening complex shown in FIG. 1, in accordance with various embodiments of the present disclosure.

With additional reference to FIG. 4, generally, the imaging station 500 comprises an opaque enclosure through which the instrumentation line conveyors 20I pass. As controlled by the screening complex control system, each test unit 26 is conveyed onto the imaging station enclosure and temporarily stopped, or positioned, at an imaging location IL, such that the respective plant is properly located within the imaging station 500 for the collection of phenotypic data. As described above, each plant and respective pot 30 is strategically positioned within the respective pot shuttle 34 at the orientation station 400. More particularly, each plant and respective pot 30 is strategically positioned within the respective pot shuttle 34 such that when the respective test unit 26 is positioned at the imaging location IL, a major horizontal axis X of each respective plant will be substantially orthogonal to an incident angle of a primary phenotypic imaging device 54 fixedly located within the imaging station 500 adjacent the instrumentation line conveyors 20I.

One or more light sources can be disposed within the enclosure to provide suitable light for imaging as required based on the type of phenotypic image data to be collected via the imaging station 500. In various embodiments, the imaging station 500 can include one or more additional imaging devices to allow more phenotypic imaging data to be collected at various angles of the respective plant. For example, in various implementations, the imaging station 500 can include a secondary phenotypic imaging device 58 mounted within the enclosure at a fixed location a particular angular distance $\beta$ (e.g., 75°) from the primary phenotypic device 54, a tertiary phenotypic imaging device 62 mounted within the enclosure at a fixed location a particular angular distance $\alpha$ (e.g., 90°) from the primary phenotypic device 54, and an overhead phenotypic imaging device 66 mounted within the enclosure substantially centered above the imaging location IL.

Once each test unit 26 is positioned at the imaging location IL within the imaging station 500, phenotypic image data is collected via the primary imaging device 54. Moreover, in various embodiments, phenotypic image data is collected via the primary imaging device 54 and the one or more additional imaging devices, e.g., the secondary, tertiary and/or overhead phenotypic imaging devices 58, 62 and/or 58. The imaging station 500 additionally includes a shuttle identification tag reader, e.g., an RFID reader, for reading the shuttle identification tag disposed on the shuttle 34 of each test unit 26 being imaged, and a data communication device, e.g., a wireless transmitter, structured and operable to communicate the acquired image data and unique identifier stored in the respective shuttle identification tag, to the screening complex control system. In various embodiments, the data communication device is included in the primary phenotypic imaging device 54 and any additional phenotypic imaging devices, e.g., the secondary, tertiary and/or overhead phenotypic imaging devices 58, 62 and/or 58. Hence, upon imaging, the collected phenotypic image data is communicated to the screening complex control system via the data communication device(s).

As described above, the phenotypic data collected within the imaging station 500 can include digital or other visible light image data, hyper-spectral image data, multi-spectral image data, electromagnetic image data, X-ray image data, and the like.

Upon receipt of the phenotypic image data received for each plant, the screening complex control system computes a biomass of each respective plant. In various embodiments, the biomass is computed using one or more statistical modeling programs executed by the screening complex control system. Such statistical modeling programs utilize a combination of phenotypic plant data such as height, width and area of plant material to compute plant biomass values. After the phenotypic image data is collected, the phenotypic image data and/or the resulting biomass computation is stored in the database and each respective test unit 26 is conveyed, via the instrumentation line conveyors 20I, from the imaging station 500 to the fertigation station 600.

In certain embodiments wherein hyperspectral image data is collected in the imaging station 500, the hyperspectral image data is transmitted to the screening complex control system wherein the control system computes the chlorophyll content and anthocyanin content of each respective plant. In various embodiments, the chlorophyll content and anthocyanin content is computed using one or more statistical modeling programs executed by the screening complex control system. After the hyperspectral image data is collected, the hyperspectral image data and/or the resulting chlorophyll and anthocyanin computations are stored in the database and each respective test unit 26 is conveyed, via the instrumentation line conveyors 20I, from the imaging station 500 to the fertigation station 600

As described above, each of the phenotypic image devices included in the imaging station 500, as described above, can be structured and operable to collect any desired type of phenotypic image data. More specifically, the imaging station 500 can be structured and operable to collect any desired type of phenotypic image data such as digital or other visible light image data, hyper-spectral image data, multi-spectral image data, electromagnetic image data, X-ray image data, etc. In certain embodiments, visible image data is collected to determine measurable characteristics of biomass, plant height, canopy area and growth rates over time for each plant. Likewise, hyperspectral image data can be collected to determine measurable characteristics of chlorophyll content and anthocyanin content for each plant.

As indicated at 920, in real-time, e.g., as each respective test unit 26 is conveyed from the imaging station 500 to the fertigation station 600, the screening complex control system analyzes the measurable characteristics determined at the weighing station 300 and the imaging station 500 to determine the treatment of each plant at the fertigation station 600. For example, the screening complex control system can analyze such characteristics as weight gain/loss data acquired at the weighing station 300, the biomass data or canopy area computed utilizing the phenotypic image data collected at the imaging station 500, and the chlorophyll content or anthocyanin score computed at the imaging station 500 to determine an amount of water and/or nutrients each respective plant should receive at the fertigation station 600 based upon the particular assay or screening program for each plant. As indicated at 924, at the fertigation station 600 each plant is provided with an amount of water and/or nutrients based on the visual, hyperspectral, and/or weight-derived measurements of the respective plant. More specifically, the screening complex control system utilizes the respective measured characteristics as inputs to compute a particular amount of water and/or nutrients to provide each plant based on the stipulated parameters of the respective screening protocol and associated assay definition template.

In various embodiments, the screening complex control system can utilize additional types of phenotypic plant data acquired via the imaging station 500 to compute a particular amount of water and/or nutrients to provide each plant based on the stipulated parameters of the respective screening protocol and associated assay definition template. For example, in various embodiments, utilizing phenotypic data acquired via the imaging station 500, e.g., digital or other visible light image data, hyper-spectral image data, multi-spectral image data, electromagnetic image data, and/or X-ray image data, the screening complex control system can determine phenotypic information for each respective plant such as plant height, canopy area, image-derived plant growth rate, plant color, chlorophyll content, anthocyanin content, water content, leaf number, leaf angle, leaf tip burn, root mass, internode length (i.e., distance between leafs), and water use efficiency. In such embodiments, the screening complex control system can utilize such phenotypic information for each respective plant as inputs to compute a particular amount of water and/or nutrients to provide each plant based on the stipulated parameters of the respective screening protocol and associated assay definition template.

The fertigation station 600 is structured and operable to dispense a controlled amount of water, e.g., reverse osmosis water, and/or a controlled amount of nutrients into the media filled pot 30 of each test unit 26 as each test unit 26 passes through fertigation station 600. More particularly, as the instrument line conveyors 20I conveys each test unit 26 through the fertigation station 600, a shuttle identification tag reader, e.g., an RFID reader, included in the fertigation station reads the shuttle identification tag disposed on the shuttle 34 of each respective test unit 26. Then, based on the identified test unit, the screening complex control system controls operation of the fertigation station 600 such that an amount of water and/or nutrients equal to that computed for each respective test unit 26, as described above, is dispensed into the media filled pot 30 of each respective test unit 26. The water and/or nutrients can be dispensed into media filled pot 30 of each test unit 26 using any suitable dispensing system structured and operable to accurately dispense the computed amounts of water and nutrients, as described above.

As indicated at 920, in real-time, e.g., as each respective test unit 26 exits the fertigation station 600, the screening complex control system determines whether the screening process for each respective test unit 26, as stipulated by the screening protocol and associated assay definition template for each respective test unit 26, has been completed.

If the screening process for a test unit 26 has not been completed, the respective test unit 26 is conveyed to the re-order station 700, via the instrumentation line conveyors 20I, as indicated at 932. The re-order station 700 includes a plant re-order subsystem 70 that comprises a plurality of re-order conveyors 70R that are controlled by the screening complex control system to randomly re-order each test unit 26 among other test units 26. More specifically, the re-order conveyors 70R are cooperatively operated to randomly shuffle or mix each newly entering test unit 26 among a plurality of other test units 26 that have previously entered the re-order station 700. After being re-ordered, each test unit 26 is returned to the assigned greenhouse 14 via the instrumentation line conveyors 20I and the greenhouse side and transverse conveyors 22S and 22T, as indicated at 936.

Hence, the re-order station 700, randomly re-orders, shuffles, or mixes, the plurality of test units 26 such that upon return to the respective greenhouse 14, each test unit 26 is in a different sequential order with respect to the adjacent test units 26 than when each respective test unit 26 exited the respective greenhouse 14 and entered the instrumentation line 20, as described above. That is, upon completion of each screening for each test unit 26, each respective test unit 26 will be returned to a different location within the respective greenhouse 14. Therefore, throughout the screening process each test unit 26 will be exposed to any climate variations that may exist within the respective greenhouse 14. More particularly, the exposure of each plant to microclimates within the respective greenhouse 14 will be reduced.

In various embodiments, the re-order station 700 receives all the test units 26 from a particular assay and re-orders the test units 26 within the respective assay and then returns the re-ordered assay to the respective greenhouse 14. The screening complex control system can utilize any suitable randomization algorithm to randomly re-order the test units 26. Additionally, as described above, in various embodiments, the position/location of each test unit 26 within the respective greenhouse 14 will also transition from the transverse conveyors 22T near greenhouse distal end 50 to the transverse conveyors 22T near the greenhouse proximal end 46.

Each test unit 26 that is returned to the respective greenhouse 14 will subsequently be conveyed to the instrumentation line 20 and undergo the weighing, orientation, imaging and fertigation at the scheduled periodic frequency as stipulated by the screening protocol and associated assay definition template for the respective test unit 26.

Alternatively, if the screening process for a test unit 26 has been completed, based on analysis of the final biomass and/or other phenotypic data obtained for each respective plant, the screening complex control system will determine whether each plant is suitable for follow-up testing, as indicated at 940.

If follow-up testing is desired, the respective test unit 26 and plant are conveyed to a plant follow-up area 850 for subsequent data collection such as tissue harvesting, as indicated at 944. For example, with regard to an exemplary WUE screening protocol, after execution of the screening protocol is complete, the water use efficiency can be calculated as the ratio of plant biomass to water provided via the fertigation station 600 over the duration of the screening. Accordingly, data points such as WUE, biomass, and plant height can be analyzed by comparing each individual transgenic event to the corresponding data for a control group assay exposed to the same environmental conditions. If the data analysis shows a desirable response to the WUE screening protocol, the respective plant will be sent to the follow-up area 850 for subsequent data collection such as tissue harvesting.

As indicated at 948, tissue samples and/or additional phenotypic and/or genotypic data can be collected for each plant conveyed to the follow-up area 850. As indicated at 948 all tissue samples are labeled and linked to the respective plant within the database, and stored for future analysis.

If follow-up testing is not desired, the respective test unit 26 and plant are conveyed to a plant discard area 800 where the plant is removed from the respective pot shuttle 34 and devitalized, i.e., destroyed, as indicated at 956. Subsequently, as indicated at 960, each pot shuttle 34 can be sterilized and stored for subsequent use in the screening complex 10, as described above.

The apparatus and methods of the present disclosure can be used to screen plants for any quantitative or qualitative trait. In various implementations, individual plants are subjected to an automated process where they are weighed, imaged and watered/fertilized on a daily basis to maintain stress levels as specified in the assay definition template. Throughout the process, data regarding various measurable characteristics is collected to enable the identification of those test plants that are significantly outperforming their matched controls in response to the imparted growth (or stress) conditions. Such data can include, but is not limited to plant height, plant width, canopy area, stem diameter, image-derived plant biomass, image-derived plant growth rate, plant color, chlorophyll content, anthocyanin content, water content, leaf number, leaf angle, leaf tip burn, root mass, internode length (i.e., distance between leafs), the amount of water applied during the growth period or induced stress period, and water use efficiency.

For example, in various embodiments, to determine the response of transgenic events under water limiting conditions, specific predetermined volumetric water content must be maintained. Water deficit is defined as a specific volumetric water content (VWC) that is lower than the VWC of non-stress plants. For instance, a non-stressed plant might be maintained at 45% VWC and a water-deficit assay might be defined around 25% VWC. The defined VWC can be held constant over the course of the assay, or it could vary from day to day.

In such embodiments, a predefined VWC can be translated into a target weight for the pot on any given day, wherein the predetermined VWC is provided in an assay definition template that is completed at the outset of each experiment. The assay definition template allows the researcher to specify the desired volumetric water content and fertilization rate provided to the plants each day. This allows complete flexibility to implement any number of water or nutrient-availability screening protocols over the course of the experiment.

After the experiment is finished, the water use efficiency (WUE) can be calculated as the ratio of plant biomass to applied water. Data points such as WUE, biomass, and plant height are analyzed by comparing each individual transgenic event to the corresponding data for the control line exposed to the same environmental conditions. For example, a test plant's T-test can be used to derive a p-value that indicates which transgenic events are significantly more tolerant than the control line with regard to water deficit stress.

The apparatus and methods of the present disclosure have been found to have particular application for the high throughput screening and physiology testing of transgenic events in a yield and stress discovery program. In particular, using the apparatus and methods of the present disclosure, one skilled in the art can introduce large numbers of gene and gene-promoter combinations into various plant genotypes for high-throughput phenotyping. Such methods allow for the rapid phenotyping and analysis to make informed decisions on field testing, lead identification, construct optimization, and even stacking strategies.

In some embodiments, the apparatus and methods of the disclosure can be used to generate a growth profile for each plant or test unit during a specified growing period. Generally, the growth profile comprises at least three measurable characteristics selected from the group consisting of plant height, canopy area, image-derived plant growth rate, plant color, chlorophyll content, anthocyanin content, water content, leaf number, leaf angle, leaf tip burn, root mass, internode length (i.e., distance between leafs), water content, the amount of water applied during the growth period, and water use efficiency. The determined growth profile for each plant can be compared to the growth profile for a positive or negative control plant or to a plant comprising a known lead gene of agronomic interest to select for plants or test subjects indicated of one or more desired traits.

Having now generally described the systems and method of the present disclosure, the same will be more readily understood through reference to the following examples which are provided by way of illustration, and are not intended to be limiting of the present disclosure, unless specified. However, those of skill in the art should, in light of the present disclosure, appreciate that many changes can be made in the specific embodiments that are disclosed and still obtain a like or similar result without departing from the spirit and scope of the present disclosure, therefore all matter set forth or shown in the accompanying drawings is to be interpreted as illustrative and not in a limiting sense.

EXAMPLE 1

This example illustrates the screening and selection of transgenic corn plants for drought tolerance.

A block of 952 plants are sown, wherein each plant is located in an individual 8 inch pot with no holes in the bottom for a vegetative, 27 day corn water deficit assay. The block is defined as an aggregate group of plants sown together at one time of like treatment and contains 56 matched nursery control plants, 8 process control plants, and 111 transgenic events comprising 8 plants per event.

Each pot is filled with soil-less media comprising 65% peat and 35% vermiculite using a potting machine to ensure uniformity in volume and compaction. The target weight of the pot plus soil is 1.5 kg.

The soil is misted with water prior to potting to provide a volumetric water content (VWC) of the soil of about 0.1 wt % water.

The pot is then placed into a shuttle including an RFID tag. The RFID tag is used to track the plant as well as for identification during data collection. Each shuttle containing a pot is conveyed to a sowing station where a single seed is placed in the pot. Here the seed ID is linked to the RFID tag of the shuttle to associate the seed ID with the respective pot retained within the shuttle.

Each shuttle having a corresponding pot with soil and planted seed (or resulting plant) retained therein will be referred to as a test unit. Each test unit is then conveyed to the instrumentation line within the headhouse where an initial weight of the test unit is collected by conveying the test unit over an inline balance/scale. Subsequently, 3 test units are conveyed to the watering station and centered below a respective one of 3 irrigation nozzles.

The specific amount of water is then added to the pot to bring soil therein to the correct VWC. The target weight of the test unit, i.e., the shuttle, pot, soil, and seed is set at 3.5 kg. The initial weight of the test unit is subtracted from a target weight to determine the amount of water to add to achieve a volumetric water content of 0.45. This VWC will be maintained for 5 days.

Prior to moving to the selected greenhouse, the test units enter a reorder buffer where their location will be randomized within the block. This occurs daily throughout the lifecycle of the plant. The test unit will then move into the selected greenhouse.

Each greenhouse contains 4 blocks of 17 conveyors that span the length of the respective greenhouse. The spacing between conveyors in each greenhouse is maintained constant through the first 3 blocks while in the fourth block they are larger to accommodate the larger plant size. The test units will matriculate to a new block each week over their 4 week life cycle, with the final week in the block with the largest spacing. Conveyors span the width of each greenhouse and hold 56 test units per conveyor.

Each day each plant, i.e., each test unit, is conveyed from the respective greenhouse and taken through the instrumentation lines.

Through day 4, the test units are conveyed from the greenhouse to the headhouse/instrumentation line where they are weighed using the inline scale and then transported to the fertigation station where a specific amount of water is added to each pot to maintain the 0.45 VWC. That amount is calculated by: Water lost (g)=Actual weight (g)−target weight (g). Each test unit is then conveyed to the reorder buffer and then back to the greenhouse.

Starting on day 5 through the rest of the lifecycle of the plant, the water added to the pots is amended with nutrients. The final nutrient solution is a 0.5× Hoagland's solution. Additionally, on day 5, the chronic water deficit stress is initiated on each plant. The target VWC is changed from 0.45 to 0.25 for the remainder of the experiment.

Beginning on day 7, after weighing each test unit, a single overhead orientation image is taken of each respective plant to determine the current orientation of the plant. The orientation image is analyzed and utilized to determine an angle of rotation necessary to orient the plant correctly for the phenotypic imaging purposes. The estimation of biomass from phenotypic images requires very precise alignment of the plant with respect to the imaging device(s), e.g., camera(s). Each test unit is then conveyed to a rotation station where the pot is rotated for the correct angle of the plant.

Each test unit is then conveyed into a phenotypic imaging station where a single overhead and three side images are taken. Particularly, a first side image is taken with the plant oriented such that the longest substantially horizontal axis of the plant, i.e., the substantially horizontal axis of the plant at the point where the plant is the widest, is substantially orthogonal to an incident angle of the imaging device. The second and third side images are respectively taken with the plant rotated counter-clockwise 75° and 90° about its vertical axis from the point of the first image. Additionally, hyperspectral images can be collected to estimate water content and chlorophyll content.

Each test unit is then conveyed to the fertigation station where the appropriate amount of water is added again to the soil to maintain a 0.25 VWC. The amount of water to be added is determined by the computer system using the following calculation: Water lost (g)=Actual weight (g)−estimated plant biomass (g)−target weight (g). The result of this calculation is then transmitted to the fertigation station. The estimated plant biomass used is the weight from the previous day in this calculation, either directly, or by extrapolating the current day's weight from the previous day.

Each test unit is then conveyed to the reorder buffer and back to the greenhouse.

On the final day, the weight of each test unit and phenotypic images of each plant are taken for biomass calculation. Then based on the results of the final biomass calculation, each plant is either sent to a follow-up area for sampling, e.g., tissue harvesting, or sent to a devitalization area for disposal.

The water use efficiency (WUE) is calculated as the ratio of plant biomass to water applied. Data points for each plant, such as WUE, biomass, and plant height, are analyzed by comparing each individual transgenic event to the corresponding data for the background line from the same greenhouse, which was included in the same experiment. A plant's T-test is used to derive a p-value that indicates which transgenic events are significantly more tolerant than the background line with regard to water deficit stress.

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. An apparatus for screening one or more potted plants for induced stress response, the apparatus comprising:
   an automated conveyor system, wherein said automated conveyor system supports and transports one or more potted plants through an automated plant screening complex;
   wherein the automated plant screening complex comprises at least one automated plant weighing station for weighing individual plants; at least one automated plant imaging station and at least one automated fertigation station; and
   a computer system that directs said automated conveyor system and said automated plant screening complex, and collects and evaluates data acquired by the at least one plant weighing station and the at least one automated plant imaging station to direct the at least one automated fertigation station to provide the one or more potted plants with a calculated amount of water, nutrients or both.

2. The apparatus as set forth in claim 1, wherein said at least one automated imaging station is operable to collect hyperspectral image data from said one or more potted plants.

3. An automated method for phenotypic screening of a population of plants, the method comprising:
   subjecting the population of plants to an induced stress in a controlled environment;
   delivering individual plants from the population of plants in the controlled environment to at least one weighing station and weighing the plants;
   delivering individual plants from the population of plants in the controlled environment to an orientation station;
   collecting a first image to determine the position of the plant in the orientation station;
   orienting the plant within the orientation station based upon the first image;
   delivering the plant to an imaging station;
   collecting at least one additional image of the plant;
   delivering the plant to a automated fertigation station; and
   evaluating, by a processor, data acquired by the at least one plant weighing station and the at least one automated plant imaging station to direct the at least one automated fertigation station to automatically provide a controlled amount of water, nutrients or a combination of water and nutrients to the plant at the automated fertigation station.

4. The method of claim 3, wherein the step of orienting the plant within the orientation station based upon the first image comprises determining the widest axis of the plant and positioning the plant such that the widest axis is aligned with an imaging device before the at least one additional image of the plant is collected at the imaging station.

5. The method of claim 3, wherein the method further comprises evaluating the image data of the plant to determine the biomass of the plant.

6. The method of claim 3, wherein the method further comprises evaluating the image data of the plant to determine the canopy area of the plant.

7. The method of claim 3, wherein the method further comprises collecting hyperspectral image data from the plant at the imaging station.

8. The method of claim 7, wherein the method further comprises evaluating the hyperspectral image data of the plant to determine the anthocyanin content of the plant.

9. The method of claim 7, wherein the method further comprises evaluating the hyperspectral image data of the plant to determine the chlorophyll content of the plant.

* * * * *